United States Patent [19]

Wiggins et al.

[11] 4,164,136

[45] Aug. 14, 1979

[54] METHOD AND APPARATUS FOR INVESTIGATING THE MOBILITY OF A SUBSTANCE

[75] Inventors: Brian H. Wiggins, Oxford; Harold D. Williams, Denham, both of England

[73] Assignee: Exxon Research & Engineering Co., Florham Park, N.J.

[21] Appl. No.: 816,803

[22] Filed: Jul. 18, 1977

[30] Foreign Application Priority Data

Jul. 16, 1976 [GB] United Kingdom .............. 29708/76

[51] Int. Cl.² .......................................... G01N 25/04
[52] U.S. Cl. .................................................. 73/17 R
[58] Field of Search ............................. 73/17 R, 64.1

[56] References Cited

U.S. PATENT DOCUMENTS

| | | | |
|---|---|---|---|
| 2,423,687 | 7/1947 | Davis et al. ................................ | 73/17 |
| 3,229,506 | 1/1966 | Bross et al. ............................... | 73/59 |
| 3,285,057 | 11/1966 | Zurik ........................................... | 73/59 |
| 3,590,627 | 7/1971 | Campbell et al. ......................... | 73/17 |
| 4,045,999 | 9/1977 | Palmer ....................................... | 73/59 |

FOREIGN PATENT DOCUMENTS

| | | | |
|---|---|---|---|
| 990697 | 4/1965 | United Kingdom ......................... | 73/17 |
| 1085607 | 10/1967 | United Kingdom ......................... | 73/17 |
| 1120925 | 7/1968 | United Kingdom ......................... | 73/59 |

OTHER PUBLICATIONS

Campbell et al., "The Automatic Determination of Pour Point", in Journ. of the Inst. of Petroleum, vol. 56, #551, 9/70, pp. 243-253.

*Primary Examiner*—Herbert Goldstein
*Attorney, Agent, or Firm*—F. Donald Paris

[57] ABSTRACT

The state of mobility of a substance—e.g., the pour point of a liquid, is determined by disposing in or in contact with the substance a shear device at the bottom end of a substantially vertical elongate probe mounted for rotation about its vertical rotational axis. The probe is urged to a datum position by suitable means (e.g. a pair of magnets) and, intermittently, a rotational force is momentarily applied to the probe at its top end to cause rotation about the probe axis away from the datum position. If the probe rotates, because the mobility of the substance so permits, a member attached to the probe interrupts a light path between a light source and a light sensor, giving rise to a signal indicative of the mobility of the substance. When there is no, or slow, rotation, the non-interruption of the light path over a selected time interval indicates a reduced mobility of the substance. The probe preferably has a temperature sensor at the bottom end for correlating mobility and temperature, and is preferably formed from a freely suspended upper part and a detachable/replaceable lower part. The two parts are mechanically and electrically connectable by a plug and socket type of connector.

19 Claims, 5 Drawing Figures

METHOD AND APPARATUS FOR INVESTIGATING THE MOBILITY OF A SUBSTANCE

The present invention relates to monitoring for determining, detecting and/or indicating the mobility or lack of mobility of a substance.

When liquids are cooled, they tend to become more viscous and less mobile, and finally they solidify. In the course of some chemical reactions, the mobility or viscosity of a liquid may change, and in the case of polymeric substances such as elemental sulphur, the mobility or viscosity increases, then decreases and finally increases again during heating.

An object of the present invention is to provide apparatus for monitoring the mobility of a liquid substance, or a change of physical state of a liquid or solid substance.

The present invention provides apparatus comprising a displaceable member suspended freely from a support member at its upper end with its longitudinal axis extending substantially vertically and having shearing means at, or near to, its lower end for contact with and/or suspension in, the substance, displacing means for applying to the displaceable member a rotary turning force which is substantially symmetrical about the longitudinal axis thereof for urging the displaceable member to turn about its longitudinal axis, means for monitoring to produce an indication whether or not the displaceable member turns or has turned about its said axis in response to the application of the rotary turning force, and means for monitoring the temperature of the substance.

The displacing means may apply the said rotary turning force either mechanically, electrically, electroinductively, magnetically, electromagnetically, hydraulically or pneumatically or by any technically realisable combination of at least two of the foregoing.

The displaceable member may be suspended from the support member by any suspension means of low torsional and/or low frictional properties such as a suspension wire, a filament of synthetic or natural origin, or a tape formed, e.g. from such wires or filaments, or a spring pivot of the type known, for example, as a flexural pivot, or low friction bearing means so that rotation of the displaceable member in response to the application of the displacing force is substantially uninfluenced by the bearing means.

One suitable bearing means may comprise a combination of two magnetic or magnetizable bodies or of a magnetic body and a magnetizable body of which one body is associated with the support member and the other with the displaceable member and which are so arranged as to repel each other and thereby eliminate or minimize contact between the displaceable member and the support member.

Another suitable bearing means comprises a bearing of the fluid type in which a fluid, such as a gas under pressure, is employed to maintain the displaceable member separated apart from the support member.

Yet another suitable bearing means comprises, associated with one of the members, an upright pin having a free upper end or tip which is smooth and of a low area and which contacts a smooth low-area bearing surface associated with the other one of the members.

Any combination of two or more of the foregoing bearing means may also be employed.

There may be provided means for constraining the displaceable member substantially to prevent turning movements thereof which are not about the said longitudinal axis. Such constraining means may operate by mechanical, electrical, magnetic, electromagnetic or fluid interaction between the displaceable member and the support member.

In one embodiment, the displacing means comprises a permanent magnet, preferably a ring magnet, attached to the displaceable member substantially symmetrically about its longitudinal axis, and an electromagnet (with or without a core) associated with the support member disposed substantially symmetrically about the axis. The electromagnet may be attached to the support member.

Preferably, suitable means are provided to urge the displaceable member to rotate, in an opposite sense to rotation caused by the displacing means, about its axis towards a datum position. Such means may be magnetizable or magnetic, e.g. a permanent magnet, which is mounted on the support member. Preferably the magnet is mounted symmetrically relative to the axis of the displaceable member, and may be a ring or bar magnet. Alternatively, the magnet may be disposed to one side of the permanent ring magnet attached to the displaceable member—this latter arrangement may be employed in some instances for convenience but is less preferred since it may tend, in some instances, to cause movement of the displaceable member at an angle to its longitudinal axis.

The displaceable member may comprise part of an assembly which turns about the longitudinal axis of the displaceable member.

Suitable means are preferably provided to prevent complete rotation of the assembly about the axis of the displaceable member. Such means may be suitable stops on the support member permitting up to, e.g. 20°, preferably up to 10°, of rotation of the assembly.

Preferably, means are provided for operating the displacing means, e.g. energizing the electromagnet(s), either at intervals of temperature of the substance or at time intervals.

There may be means for monitoring, indicating and/or recording the temperature at which the assembly is either prevented from rotating at least from one selected position to another selected position at least over a selected time period due to low or nil mobility of the substance and/or at which the assembly becomes free to rotate due to an increase in mobility or melting of the substance.

Preferably, a device for sensing the temperature of the substance is located, or attached, to or in the displaceable member at or near its lower end.

The assembly may comprise an arm which is arranged to actuate means for indicating, monitoring and/or recording that the arm is substantially movable or immobilized due, e.g. to the interaction of the shearing means with the substance. Such means may comprise a source of light on one side of the plane in which the arm moves, a sensor on the other side of said plane for receiving light from said source and a part of the arm adapted to interrupt the light path between the source and the sensor when the assembly is in a selected rotational position, e.g. the said datum rotational position. Preferably, the datum position of the assembly corresponds to a state of low or nil mobility of the substance when in contact with the shearing means.

Preferably, the temperature at which there is a significant change in the mobility of the substance is detected, monitored, recorded and/or displayed.

The apparatus may comprise means for heating and/or cooling the substance. There may also be automatic means for reversing the operative state of the heating/cooling means when a significant change of mobility of the substance is detected so that, should such a change be reversible and temperature dependent, the substance will be heated or cooled (as the case may be) to pass in the reverse sense through the temperature or temperature range at which the mobility change occurs. The temperature at which a substantial or significant mobility change occurs in the reverse sense may also be monitored. The cycle of heating and cooling the substance may be repeated a selected number of times.

The device for sensing the temperature of the substance is preferably an electrical resistance thermometer or a thermocouple element or other device having electrical properties which vary with temperature. The temperature-related electrical signal obtained from such a device is preferably conducted from the region of the shearing member through the displaceable member to the vicinity of the upper end of the displaceable member, and from the upper end through one or more conducting elements attached directly or indirectly to the support member or other non-movable part, the conducting elements being of such low rigidity that they exert substantially no mechanical resistance to rotational movement of the assembly about the longitudinal axis of the displaceable member.

Preferably, the displaceable member comprises a first part, including the said upper end, and which is preferably substantially permanently attached to the assembly which preferably comprises the displacing means, and a second part having the shearing means thereon which is readily detachable from, and attachable to, or replaceable by, a different second part having, e.g., a differently sized and/or shaped shearing member and/or temperature sensing device. The parts may be connected mechanically and electrically by a plug and socket type connector in which the plug comprises an electrically conductive pin or like protruding member surrounded by a spaced-apart electrically conductive sleeve, the socket comprising an inner conductive sleeve for receiving and engaging the pin and a surrounding, spaced-apart outer conductive sleeve for engaging with the conductive sleeve of the plug, the engagement of the pin and sleeve being effected by a number of circumferentially separated conductive elements or strips which define or form a divergent-convergent-divergent envelope within the plug and/or socket and which are outwardly deformed (e.g. radially outwardly) on connecting the plug and socket thereby to grip, and form mechanical and electrical connections between, the lower and upper parts of the displaceable member.

The elements may be wires or metal strips which are either (a) substantially straight or radially inwardly bowed, extending at an acute angle to the axis of the connector parts, or (b) radially inwardly bowed and substantially parallel to the axis of the connector parts.

In a preferred embodiment, a plurality of conductive elements are disposed on the inside of the inner sleeve of the socket and a plurality of conductive elements are disposed on the inside of the sleeve of the plug so that when the plug and socket are connected, the elements on the inner sleeve of the socket mechanically and electrically engage the outer surface of the outer sleeve of the socket. Preferably, electrical insulation separates the inner and outer sleeves of the socket to prevent short circuiting within the socket.

Electrical connections are preferably made to the connector via the interior of the parts of the displaceable member. The electrical conductor(s) from the temperature sensing device are preferably enclosed or encased within a sheath of low thermal conductivity material such as rubber, resin or plastics material.

Embodiments of the invention, given by way of non-limitative example only, are now described with reference to the accompanying drawings, in which:

FIG. 3 shows a plug and socket connector employed in the apparatus of FIGS. 2 and 2a.

Figure 1:
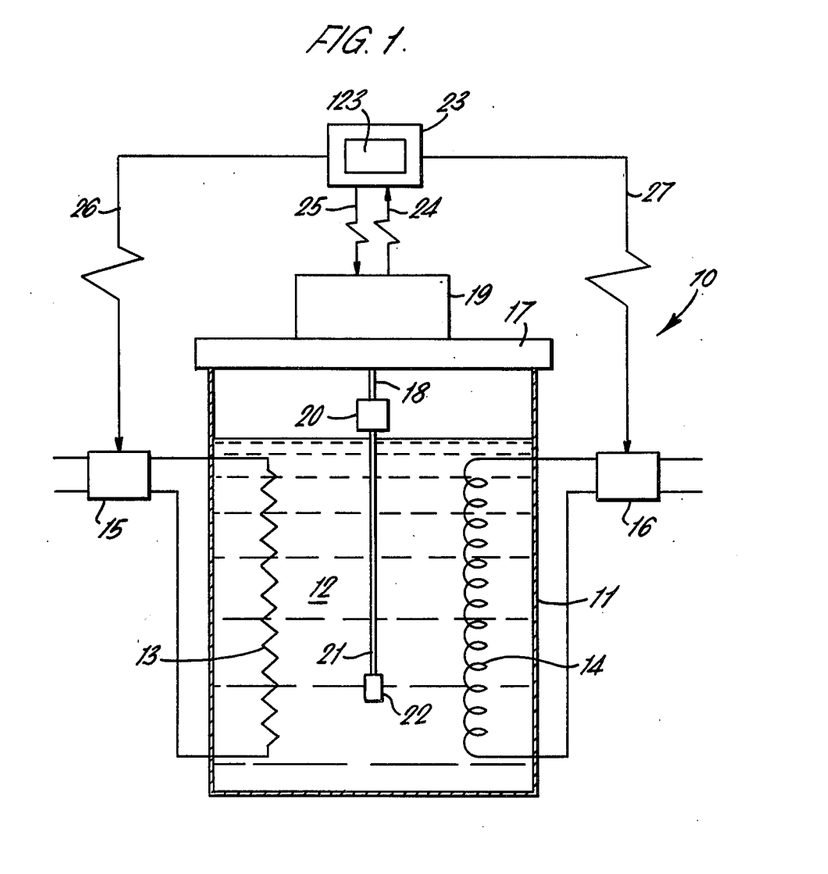
FIG. 1 is a diagrammatic vertical cross-sectional view of equipment embodying the invention.

FIGS. 1 shows an apparatus for determining the pour point of a hydrocarbon liquid. The apparatus, generally indicated by 10, comprises a container 11 for containing the liquid 12. The liquid 12 may be heated by a heater 13 and cooled by a cooler 14. The heater 13 and cooler 14 may be provided by a thermoelectric pack operating on the Peltier effect, or the heater 13 may be an electrical resistance heater or coils for the passage of a hot fluid (e.g. hot water) and/or the cooler 14 may comprise coils through which a cooling fluid (e.g. a refrigerant from a conventional refrigerating system) is passed. The heater 13 is controlled from a regulator 15 and the cooler 14 is controlled from a regulator 16.

The open top of the container 11 is closed by a lid, and the lid may be comprised of, or consist of, a support member 17 formed of a relatively rigid plastics material such as Tufnol ("Tufnol" is a registered trade mark). The support member 17 has a central orifice therethrough (not visible in FIG. 1) through which downwardly protrudes a probe holder 18 which is rotatably suspended from an actuating mechanism depicted as a box 19. The lower end of the probe holder 18 has a socket of a plug and socket connector 20 by means of which a probe 21 having the plug of the connector 20 is mechanically and electrically engaged with the probe holder 18.

The probe 21 has an external shearing device, shown as a vane 22, which, on the application of a displacing force thereto, will be displaced in the liquid a distance depending on the mobility of the liquid 12. If the liquid 12 has been, e.g. so cooled or otherwise treated, that it has congealed or become solid, the application of a displacing force to the vane 22 will cause no or only insignificant movement.

If it is required to monitor the mobility of the liquid 12 (or solidified liquid) as the liquid (solid) is heated or cooled, a temperature sensing device is located in contact with the liquid (solid), and the temperature readings correlated with the mobility of the liquid. Preferably the temperature sensor is located in the probe 21 in the vicinity of the vane 22 or other shearing device. A preferred temperature sensor is a resistance thermometer or thermocouple which is electrically connected by conductors via the connector 20 to an indicating, recording and/or monitoring and control device 23. Signals representative of temperature are conducted to the control device 23 by line 24. For accurate monitoring of the mobility of the liquid 12, and of changes therein, a displacing force is applied to the shearing vane 22 at selected intervals of temperature—e.g. at every 3° C. or 5° F. The control device 23 automatically sends a signal, via line 25, to the actuating mechanism 19 at every 3° C. or 5° F. temperature interval, to apply a displacing force to the shearing vane 22. The rate of heating and cooling, and whether the liquid should be heated or cooled is also regulated and/or regulatable from the control device 23 which, in accordance with a predetermined programme, sends appropriate signals to the regulators 15 and 16 via lines 26, 27. Thus, the control device may be so programmed or otherwise arranged that the liquid is cooled by the cooler 14 until its mobility is so low that substantially no movement of the shearing vane occurs on application of the displacing force thereto and that when this state has been noted at the control device, a signal may be sent to the regulator 16 to stop the cooling by the cooler 14. A signal may also be sent to the regulator 15 to initiate and maintain heating by the heater 13. When the mobility of the liquid has increased to a value permitting a predetermined maximum displacement of the vane 22 to take place on application of the displacing force thereto, and/or when the temperature of the liquid attains a selected value, e.g. 115° F. (46° C.), the control device 23 interrupts the heating and initiates the cooling of the sample, thereby repeating the cycle. There may be provided a dial or dials and/or digital display showing information such as the temperature(s) at which a particular mobility or lack of mobility commenced, the part of the operating cycle that the equipment is in at each instant, etc. The dial(s) display are indicated as item 123 in FIG. 1. Of course, they need not be located on the control device 23 as indicated. Preferably, the temperature signals received from the sensing device are converted to binary digital signals so that they can be both displayed on a suitable digital display device and employed to regulate the operating cycle.

In practical embodiments, the heater 13 and cooler 14 are preferably cylindrical coils concentric with the probe 21 and the coils may be of the same diameter and axial length.

Figure 2:
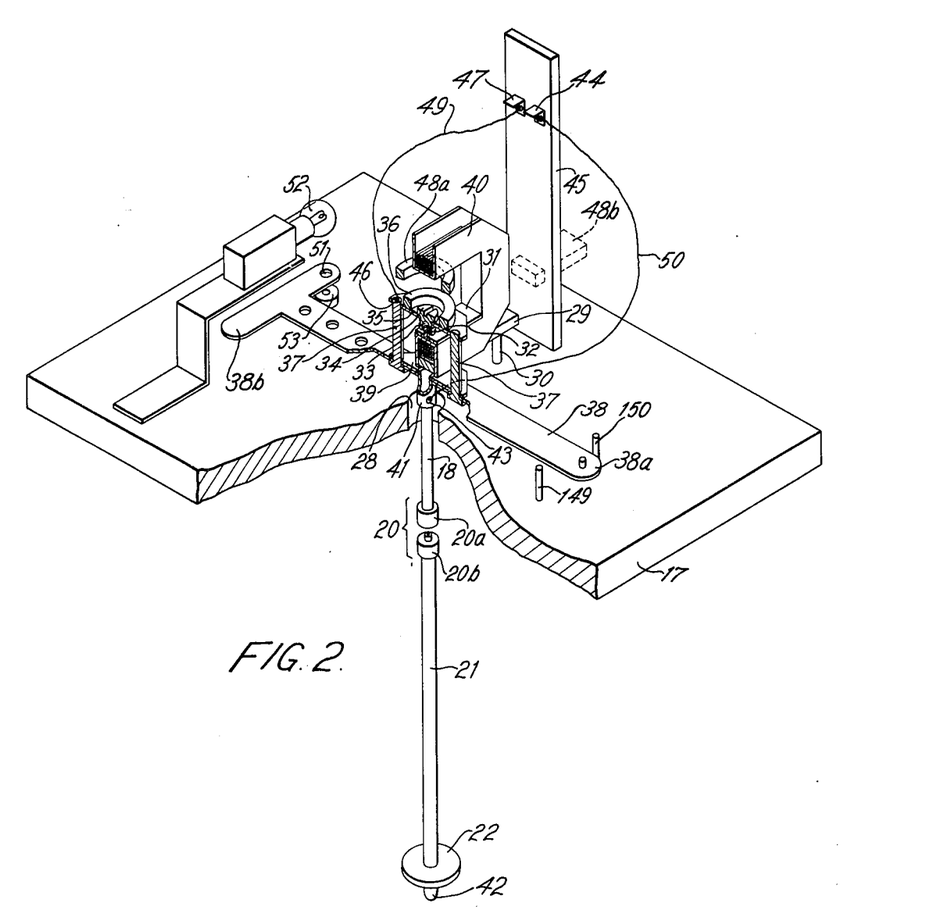
FIG. 2 is a perspective view, with parts broken away, of apparatus used in the equipment of FIG. 1.

Reference is now made to FIG. 2 wherein there is depicted the support member 17 in the form of a Tufnol plate having an orifice 28 therethrough. A bridge piece 29 supported on pillars 30 (only one being shown in FIG. 2) extends over the aperture 28 and is spaced from the plate 17. An electromagnet coil 40 is attached on the top of the bridge piece 29 with its axis substantially horizontal, and a brass support plate 31 fixed to the upper side of the lower part of the coil has an upright pin 32 having a smooth, part-spherical tip protruding from the upper side thereof. A recess 33, having a smooth end-bearing of, e.g. agate, formed in the bottom of a screw 34 surrounds the top of the pin 32 so that the screw 34 is free to rotate with the smooth end-bearing of the recess on, and contacting, the smooth, part-spherical free end tip of the pin, and the screw is threaded to a plate 35 to which is secured a permanent ring magnet 36 on its upper surface at approximately the height of the axis of the electromagnet coil 40 and coaxial with the pin 32 so that on energization of the coil 40, the ring magnet 36 will be rotated around the axis of the pin 32 to a selected position. Two pillars 37 are secured to the plate 36 on opposite sides of the screw 34 and are attached at their bottom ends to an arm located between the bridge piece 29 and the support plate 17. The arm 38 has an aperture therethrough which is coaxial with the axis of the pin 32 and with the axes of the apertures in the support plate 17 and the bridge piece 29. A retaining member 39 is attached on the upper face of the arm 38 and a brass tube 41 extends downwardly from the retaining member 39 through the aperture 28 wherein a narrower brass tube constituting the probe holder 18 of FIG. 1 is received. The probe holder 18 has a socket connector 20a which engages and makes electrical contact with a plug connector 20b at the top end of the probe 21 which is hollow and made of an inert, thermally insulating material such as Tufnol. The probe has a shearing member in the form of a disc 22 and immediately below the disc 22 is a stainless steel cup 42 containing a platinum resistance temperature sensor (not shown). The sensor is connected by a pair of electrical conductors (not visible in the drawings) within the probe 21 to appropriate parts of the connector 20a, 20b as described below, and by one conductor within the brass probe holder 18 and extending through an aperture 43 in the brass tube 41 to a terminal 44 on a Tufnol mounting plate 45. The other electrical conductor is "earthed" to the probe holder 18 and a connection is made from a point 46 on one of the pillars 37 to a terminal 47 on the mounting plate 45. The connection to the terminals 44, 47 is by relatively long, thin wires 49, 50 which will exert an insignificant torque or mechanical resistance to movement on the probe holder 18 when the latter is turned through relatively small angles (say, up to 20°) about the axis of the pin 32.

A permanent magnet is employed to provide a restoring force to urge the probe 21 and parts attached thereto, such as the arm 38 in particular, to a datum position. The restoring magnet is arranged to attract the ring magnet 36 to a position corresponding to the datum position of the parts attached thereto.

As shown in FIG. 2, the restoring force is furnished by a ring magnet 48a attached in any convenient manner (not shown) to the coil 40, above and co-axial with, the ring magnet 36. The poles of the magnets 36 and 48a are so arranged as to maintain or urge the magnet 36 and parts attached thereto to rotate on the pin 32 to a datum position determined by one end 38a resting against one of two upright posts 149 and 150 fixed to the plate 17.

Instead of employing a co-axial ring magnet 48a, there may be used a bar magnet 48b (shown in broken lines) located in the mounting plate 45 at substantially the same horizontal level as the ring magnet 36. A slight drawback of this arrangement is that the horizontal attraction of the magnets 36 and 48b causes a degree of tilting of the probe 21 from the vertical, and the rotational movements of the probe 21, during use of the apparatus may not then be truly about the rotational axis of the probe 21 when the latter moves from and to its datum position.

Figure 2A:
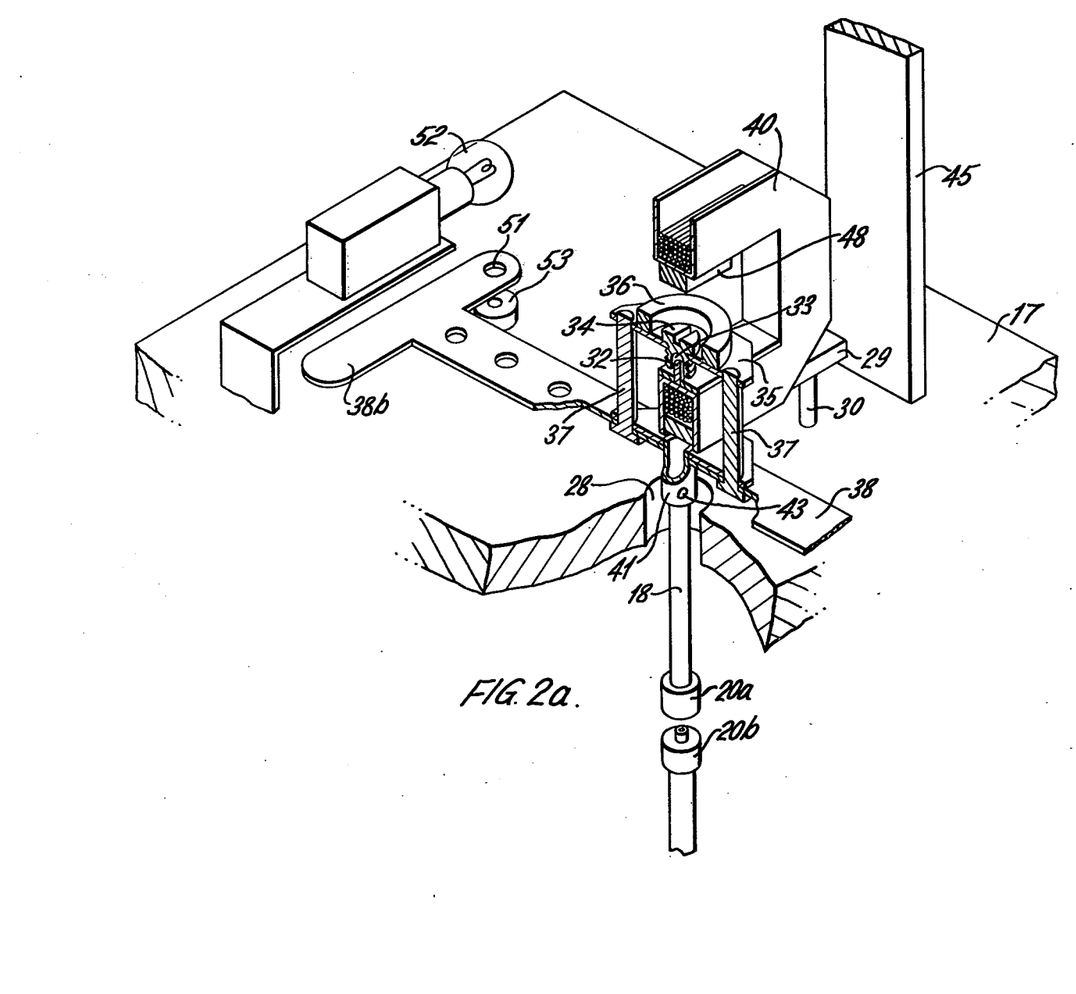
FIG. 2a shows, to a larger scale, part of the apparatus of FIG. 2 with a modification.

In FIG. 2a, the permanent magnet is a bar magnet 48 attached to the coil 40 in any convenient way so as to be symmetrically disposed relative to the vertical rotational axis of the probe. The poles of the bar magnet 48 are so arranged as to urge the ring magnet 36 and the parts attached thereto to the datum position (as described in relation to FIG. 2) by rotation on the pin 32, or to maintain the magnet 36 and attached parts in the datum position. From the point of view of cost, the bar magnet 48 may be preferred to the ring magnet 48a of FIG. 2.

In FIGS. 2 and 2a, the arrangement of the ring magnet 36 and the electromagnet 40 is such that when the latter is energized, the ring magnet 36 is caused to rotate about the axis of the pin 32 causing concomitant rotation of the arm 38, probe holder 18 and probe 21 until the other of the two upright posts 150 or 149 arrests the arm 38. The angle between the extreme positions of the arm 38, as determined by the posts 149 and 150, is 10° or thereabouts.

The other end 38b of the arm 38 is in the form of a "T" and has an aperture 51 therethrough in one extremity thereof. A lamp 52 (or other convenient source of light) is disposed above the end 38b at such a position that light will pass vertically through the aperture 41 only when the arm 38 is in its datum (i.e. undeflected) position. Vertically beneath the lamp 52 is a light sensor 53 which, during operation, receives light only when the aperture 41 is interposed between the lamp 52 and the sensor 53 in the datum position.

Figure 3:
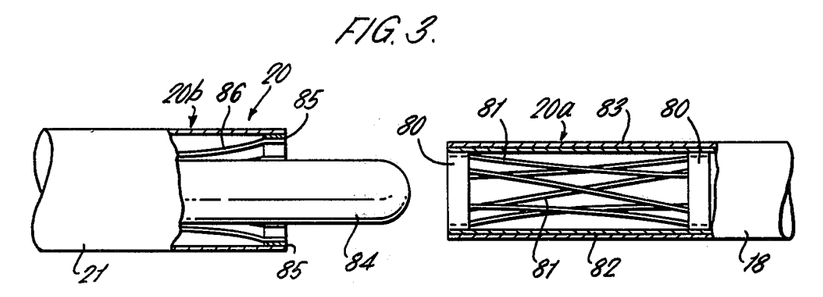
Figure 4:
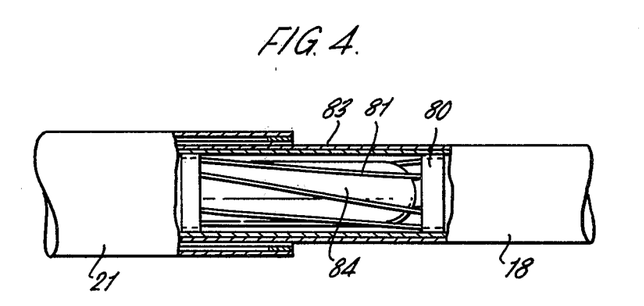
FIG. 4 shows the plug and socket connector of FIG. 3 when connected.

Reference is now made to FIGS. 3 and 4 which show the main features of the plug and socket connector 20.

The socket 20a is shown as integral with the probe holder 18 and the plug 20b is shown integral with the probe 21, but it will be appreciated that they could be arranged in the opposite way round.

The socket 20a comprises an electrically conductive inner sleeve 80 (of which the two end portions only are shown for clarity of illustration) having attached to its axial ends thereof a plurality of springy and/or resilient electrically conductive elements 81 (such as wires or metal strips).

Preferably, the elements 81 are of, or covered by, a material such as gold which has a consistently low electrical contact resistance. The elements 81 may be attached to the sleeve 80 by brazing and/or by being hooked over the axial ends of the sleeve, and may be inwardly bowed. The elements 81 are disposed inwardly of the sleeve 80 and extend from one end to the other at an acute angle to its axis so that the envelope defined by the elements is convergent towards the central radial plane of the sleeve 80. A non-conductive cylindrical sleeve 82 surrounds the sleeve 80, and an electrically conductive sleeve 83 surrounds the sleeve 82 and forms the outer part of the socket 20a. The sleeves 80 and 83 are connected to electrical conductors (not shown) within the probe holder 18, which conductors correspond with the wires 49 and 50 shown in FIG. 2.

The plug 20b comprises a central pin 84 surrounded by an electrically conductive sleeve 85 (of which only one end is shown). The sleeve 85 defines an annular space around the pin 84, and a number of springy and/or resilient electrically conductive elements 86, such as wires or metal strips, are attached to the axial ends of the sleeve 85 by brazing and/or by being hooked over the ends at an acute angle to its axis. The elements 86 may be inwardly bowed, as exaggeratedly shown. The envelope of the elements 86 is convergent towards the central radial plane of the sleeve 85, but none of the elements 86 touches the pin 84. The pin 84 and sleeve 85 are separately connected to electrical conductors (not shown) within the probe 21 which are connected to the sensing element in the cup 42 (shown in FIG. 2).

The dimensions of the components of the plug and socket are such that when the two are engaged, as shown in FIG. 4, the pin 84 is received in the sleeve 80 of the socket and engaged and gripped by the elements 81 which tend to be deformed by the pin. The outer sleeve 83 of the socket is engaged and gripped on its outer surface by the elements 86 of the plug, and the elements 86 tend to be outwardly deformed by the sleeve 83. The engagement of the plug 20b and 20a is mechanically and electrically firm, reliable and substantially repeatable so far as its mechanical and electrical properties are concerned, and permits repeated separation and engagement without significant changes in the mechanical or electrical properties of the connector 20. If a different probe is to be used, the same mechanical and electrical reliability will be obtained provided the said different probe has a plug 20b of the type described.

In the operation of the apparatus embodying the invention, the terminals 44 and 47 and the sensor 53 are connected to the control device 23 and/or to the monitoring, detecting and/or display device 123 of FIG. 1, and electrical power is supplied to the control device 23 for energizing the device and for powering the electromagnet 40, and the regulators 15 and 16.

In the determination of e.g. the pour point of a hydrocarbon liquid, the operation of the apparatus 10 is broadly as follows:

A probe 21 having a shear disc 22 of appropriate size for the liquid is connected to the probe holder 18 by the plug and socket connector 20. The liquid is disposed in the container 11 and the probe 21 suspended therein more or less as schematically shown in FIG. 1. The temperature of the liquid is reduced by appropriate operation of the cooling regulator 15 and every 3° C. (or 5° F.), as determined by the temperature sensor in the cup 42 at the bottom of the probe 21 and/or every 2 minutes in accordance with the operation of a suitable timing device, an electrical energizing pulse is imparted to the electromagnet 40 to generate a displacing force tending to rotate the ring magnet 36, the probe 21, and other components assembled thereto, about the axis of the mounting pin 32, against the restoring force provided by the interaction of the ring magnet 36 and bar magnet 48. If a light signal is not received by the control device 23 from the light sensor 53 after the electromagnet has been energized (indicating that the arm 38 has swung away from and then returned to its datum position), the cooling is continued and further pulses energize the electromagnet 40 to displace the probe in the liquid.

When the liquid is at or slightly below its pour point, the probe 21 will no longer rotate about its axis on excitation of the electromagnet 40 from the datum point set by the interaction of end 38a of arm 38 with post 50. The time interval during which a light-indicating signal from the sensor 53 persists then exceeds a predetermined time known to correspond to time intervals indicative of the liquid being above its pour point thereby indicating that the temperature of the liquid is no more than its pour point temperature. The temperature at which the excessively long time interval (e.g. 5 seconds) is achieved may be displayed by the dial or digital display panel of device 123.

The control device 23 may incorporate means for recording the pour point temperature, and may optionally comprise automatic switching means for operating the regulator 16 to stop cooling the liquid when the pour point has been reached and for operating the regulator 15 to initiate heating of the liquid to a standard temperature such as 115° F. (46° C.) for a further test. During the heating part of the cycle, the electromagnet may be excited every 3° C. or 5° F. and/or 2 minutes and the lower temperature at which relatively free part-rotational displacement of the probe 21 corresponding to the angle between the posts 49, 50 commences may be displayed, indicated and/or recorded by device 123, if desired. This lowest temperature will tend to be about the same as the pour point as determined during the cooling part of the cycle. The control device may be programmed to inactivate the heating and initiate cooling by switching off regulator 15 and switching on regulator 16 so as to commence further cycles of cooling and heating.

What we claim is:

1. Apparatus for use in determining the pour point of a substance, comprising: a displaceable elongated rigid member suspended freely from a support member at its upper end and having its longitudinal axis extending substantially vertical; shearing means at the lower end of said displaceable elongated member for suspension in the substance; displacing means connected for applying a rotary turning force to said displaceable elongated member in a substantially symmetrical relationship about said longitudinal axis thereof for urging said displaceable member to turn at least a limited amount about said longitudinal axis; means for connecting said displaceable member with said displacing means such that said displaceable member is constrained to only substantially concentric turning movement about said longitudinal axis such that there is no substantial angular movement of said displaceable member relative to the longitudinal axis thereof; means for preventing complete rotation of said displaceable member about said longitudinal axis and permitting movement in only a predetermined range; means for causing said displaceable member to return to the same datum position after each determination of said pour point; means for causing said displacing means to operate at predetermined selected intervals for actuating said turning of said displaceable member; and means for monitoring the temperature of said substance.

2. Apparatus according to claim 1 in which the displaceable member is suspended from the support member by suspension means of low torsional and low frictional properties.

3. Apparatus according to claim 1 in which the displaceable member comprises part of an assembly which is rotatable with the displaceable member about the longitudinal axis of the latter.

4. Apparatus according to claim 1 wherein said monitoring means comprises a temperature-sensing device located at the lower end of the displaceable member.

5. Apparatus according to claim 4 wherein said monitoring means comprises temperature-signal conductive elements connected at one end to the displaceable member and at the other end to a stationary part of the apparatus, said elements being of such low rigidity that they exert substantially no mechanical resistance to rotational movement of the displaceable member.

6. Apparatus according to claim 1 comprising means for heating and/or cooling the substance.

7. Apparatus according to claim 1 wherein said displacing means applies an electromagnetic rotary turning force to said displaceable member.

8. Apparatus according to claim 1 wherein said restoring means causes said displaceable member to rotate about its axis toward said datum position, in a rotational sense opposite to the direction of rotation induced by said displacing means.

9. Apparatus according to claim 1 wherein said means for monitoring the temperature of said substance provides indication at which said displaceable member changes its rotational characteristic about its longitudinal axis from said datum position to a further position over a predetermined period of time as a result of changes in the state of pour point of said substance in which said lower end of said displaceable member is disposed.

10. Apparatus according to claim 9 including an arm attached with said displaceable member arranged for actuating indicating means for indicating whether or not said displaceable member is rotating between within said selected positions over said selected period of time.

11. Apparatus according to claim 10 in which said indicating means comprise a source of light on one side of the plane in which the arm moves, a sensor on the other side of said plane for receiving light from said source and a part of the arm constructed and arranged to interrupt the light path between the source and the sensor when the displaceable member is in a selected rotational position.

12. Apparatus according to claim 11 in which the selected rotational position said datum position of the displaceable member.

13. Apparatus according to claim 1 wherein said displaceable member comprises a first part having an upper end rotatably mounted with respect to a fixed assembly which includes said displacing means and said displaceable member having a second part for mounting said shearing means which is removably mounted therewith.

14. Apparatus according to claim 13 wherein said first and second parts are detachably connected by a plug and socket connection.

15. Apparatus for use in determining the pour point of a substance, comprising: a displaceable elongated member suspended freely from a support member at its upper end and having its longitudinal axis extending substantially vertical; shearing means at the lower end of said displaceable elongated member for suspension in the substance; displacing means connected for applying a rotary turning force to said displaceable elongated member in a substantially symmetrical relationship about said longitudinal axis thereof for urging said displaceable member to turn at least a limited amount about said longitudinal axis, said displacing means comprising a permanent magnet attached to said displaceable member substantially symmetrically about said longitudinal axis thereof, and an electromagnet associated with said support member disposed substantially symmetrically about said longitudinal axis; means for connecting said displaceable member with said displacing means such that said displaceable member is constrained to substantially concentric turning movement about said longitudinal axis; means for preventing complete rotation of said displaceable member about said longitudinal axis and permitting movement in only a predetermined range; means for causing said displaceable member to return to the same datum position after each determination of said pour point; means for causing said displacing means to operate at predetermined selected intervals for actuating said turning of said displaceable member; and means for monitoring the temperature of said substance.

16. Apparatus for use in determining the pour point of a substance, comprising: a displaceable elongated member suspended freely from a support member at its upper end and having its longitudinal axis extending substantially vertical; shearing means at the lower end of said displaceable elongated member for suspension in the substance; displacing means connected for applying a rotary turning force to said displaceable elongated member in a substantially symmetrical relationship about said longitudinal axis thereof for urging said displaceable member to turn at least a limited amount about said longitudinal axis; means for connecting said displaceable member with said displacing means such that said displaceable member is constrained to substantially concentric turning movement about said longitudinal axis; means for preventing complete rotation of said displaceable member about said longitudinal axis and permitting movement in only a predetermined range; restoring means comprising magnetic means operably associated with said support member for causing said displaceable member to rotate about its axis and return to the same datum position after each determination of said pour point wherein said rotational movement is in a sense opposite to the direction of rotation induced by said displacing means; means for causing said displacing means to operate at predetermined selected intervals for actuating said turning of said displaceable member; and means for monitoring the temperature of said substance.

17. Apparatus for use in determining the pour point of a substance, comprising: a displaceable elongated member suspended freely from a support member at its upper end and having its longitudinal axis extending substantially vertical, wherein said displaceable member is suspended from said support member by suspension means of low torsional and low frictional properties; said suspension means including bearing means which comprises an upright pin having an upper tip which is substantially smooth associated with one of said displaceable member and said support member, and a lower substantially smooth bearing surface in operable contact with said tip and associated with the other of said members; shearing means at the lower end of said displaceable elongated member for suspension in the substance; displacing means connected for applying a rotary turning force to said displaceable elongated member in a substantially symmetrical relationship about said longitudinal axis thereof for urging said displaceable member to turn at least a limited amount about said longitudinal axis; means for connecting said displaceable member with said displacing means such that said displaceable member is constrained to substantially concentric turning movement about said longitudinal axis; means for preventing complete rotation of said displaceable member about said longitudinal axis and permitting movement in only a predetermined range; means for causing said displaceable member to return to the same datum position after each determination of said pour point; means for causing said displacing means to operate at predetermined selected intervals for actuating said turning of said displaceable member; and means for monitoring the temperature of said substance.

18. Apparatus for use in determining the pour point of a substance, comprising: a displaceable elongated member suspended freely from a support member at its upper end and having its longitudinal axis extending substantially vertical wherein said displaceable member comprises a first and a second part detachably connected by a plug and socket connection, wherein said plug comprises an electrically conductive protruding member surrounded by a spaced electrically conductive sleeve and said socket comprises an inert conductive sleeve for receiving and detachably engaging said protruding member, an outer conductive sleeve surrounding and spaced from said inner conductive sleeve of said socket for detachably engaging said conductive sleeve with said plug, and a plurality of circumferentially spaced, electrically conductive elements which define an envelope of predetermined configuration for engaging and being deformed upon connection of said plug and said socket, whereby said first and said second parts are mechanically and electrically connected; shearing means at the lower end of said displaceable elongated member for suspension in the substance; displacing means connected for applying a rotary turning force to said displaceable elongated member in a substantially symmetrical relationship about said longitudinal axis thereof for urging said displaceable member to turn at least a limited amount about said longitudinal axis, wherein said displaceable member comprises said first part which has an upper end rotatably mounted with respect to a fixed assembly which includes said displacing means and said displaceable member having a said second part for mounting said shearing means which is removably mounted therewith; means for connecting said displaceable member with said displacing means such that said displaceable member is constrained to substantially concentric turning movement about said longitudinal axis; means for preventing complete rotation of said displaceable member about said longitudinal axis and permitting movement in only a predetermined range; means for causing said displaceable member to return to the same datum position after each determination of said pour point; means for causing said displacing means to operate at predetermined selected intervals for actuating said turning of said displaceable member; and means for monitoring the temperature of said substance.

19. Apparatus according to claim 18 wherein said plurality of conductive elements are disposed on the inside of said inner sleeve of said plug such that upon connection of said plug and said socket, said elements mechanically and electrically engage said outer surface of said outer sleeve of said socket.

* * * * *